United States Patent [19]

Barlow et al.

[11] Patent Number: 4,499,013

[45] Date of Patent: Feb. 12, 1985

[54] ELECTRICAL TREE AND WATER TREE RESISTANT COMPOUNDS AND POLYMER COMPOSITIONS CONTAINING THE SAME

[75] Inventors: Anthony Barlow; Irwin S. Schlossman; Robert E. Borgerding, all of Cincinnati, Ohio

[73] Assignee: National Distillers and Chemical Corporation, New York, N.Y.

[21] Appl. No.: 524,003

[22] Filed: Aug. 17, 1983

[51] Int. Cl.$^3$ ............................................. H01B 3/18
[52] U.S. Cl. .................................... 252/567; 252/570; 560/51; 560/52; 562/459; 562/460; 568/332; 568/335; 568/336; 568/338
[58] Field of Search ................. 252/567, 570; 560/51, 560/52; 562/459, 460; 568/338, 332, 335, 336

[56] References Cited

U.S. PATENT DOCUMENTS

| | | | |
|---|---|---|---|
| 4,206,260 | 6/1980 | McMahon | 524/385 |
| 4,263,158 | 4/1981 | Ashcraft et al. | 524/237 |
| 4,299,713 | 11/1981 | Maringer et al. | 524/560 |
| 4,354,992 | 10/1982 | Bahder | 264/174 |
| 4,400,429 | 8/1983 | Barlow et al. | 428/379 |

FOREIGN PATENT DOCUMENTS

| | | |
|---|---|---|
| 2737430 | 2/1979 | Fed. Rep. of Germany . |
| 1248256 | 9/1971 | United Kingdom . |
| 1277378 | 6/1972 | United Kingdom . |

OTHER PUBLICATIONS

Nobuichi et al. C.A. vol. 89, 180894p, 1978.

Primary Examiner—John E. Kittle
Assistant Examiner—Mukund J. Shah
Attorney, Agent, or Firm—Kenneth D. Tremain; Gerald A. Baracka

[57] ABSTRACT

Certain fatty acids, esters and alcohol derivatives useful as electrical tree and water tree resistant compounds in polymer compositions are disclosed.

13 Claims, No Drawings

ELECTRICAL TREE AND WATER TREE RESISTANT COMPOUNDS AND POLYMER COMPOSITIONS CONTAINING THE SAME

BACKGROUND OF THE INVENTION

This invention relates to novel substituted fatty acids and ester or alcohol derivatives thereof and polymeric compositions containing said substituted fatty acids or derivatives having increased resistance to electrical treeing and water treeing, said compositions being useful as insulation for electrical cable.

Polymeric compositions are well-known and are used extensively as insulation materials for wire and cable. As an insulator, it is important that the composition have various physical and electrical properties, such as resistance to mechanical cutthrough, stress crack resistance and resistance to dielectric failure. Recent publications have indicated that water tree growth and electrical tree growth in the insulation are particularly important problems since they are associated with, though not necessarily totally responsible for, dielectric failure.

An important application for an insulation material is in high voltage transmission and distribution cable, especially in direct buried underground service and three types of trees have been observed in power cables, to wit, electrical trees, water trees and electrochemical trees. It is generally believed that electrical trees are generated by corona discharges causing fusion and breakdown of the polymer, whereas water trees are usually observed in cables buried in wet locations and have a different appearance compared to the electrical trees. The electrochemical trees are similar to the water trees but are characterized by the presence of metal ions in the trees.

U.S. Pat. No. 4,144,202 granted to Ashcraft et al. relates to inhibiting the electrical breakdown of insulation by water treeing in dielectric materials based on ethylene polymers. This patent discusses electrical failures which are due to treeing and explains the concept of treeing and some of the causes for treeing. In general, as the polymeric composition breaks down the damage progresses through the insulator, or dielectric, in a path that looks something like a tree. Treeing usually is a slow type failure and may take years to cause a failure in the insulation. As disclosed in the patent, water treeing is inhibited in the ethylene polymer compositions by employing therein certain organo silane compounds. In particular, the organo silane is a silane containing an epoxy containing radical. Suitable polymers, adjuvants and processing procedures for preparing the compositions are described in the patent, which patent is hereby incorporated by reference.

U.S. Pat. No. 4,206,260 granted to McMahon relates to insulation particularly suitable for high voltage power cable containing an effective amount of an alcohol of 6 to 24 carbon atoms which imparts electrical tree growth resistance to the composition. This patent, as in U.S. Pat. No. 4,144,202, supra, contains a discussion of the electrical treeing problem in polymer compositions and cites numerous patents attempting to overcome this problem. Suitable polymers, adjuvants and preparation procedures are noted therein and this patent is hereby incorporated by reference.

German Offenlegungsschrift No. 2,737,430 discloses that certain alkoxysilanes added to polyolefin insulation prevent water-tree formation. Several trimethoxy and triethoxy silanes are said to be useful.

U.S. Pat. No. 3,553,348 granted to Betts, British Pat. No. 1,248,256 granted to General Electric Company and British Pat. No. 1,277,378 granted to General Electric Company relate to mineral filled polymer compositions useful as electrical wire and cable insulation. The mineral filler is treated with an organosilane such as an alkyl alkoxysilane or a vinyl alkoxysilane to decrease the porosity of the composition.

In addition, it is known that long chain fatty acids show evidence of good water tree retardancy but rather poor electrical tree retardancy. Their effect on the dielectric properties of the polymer insulation is variable depending upon the structure of the fatty acid. Some of the fatty acids and their derivatives, e.g. phenylstearic, tolyl-stearic, do not produce the adverse effect on the dielectric properties noted with some organic silanes. The fatty acids can, however, "bloom" or diffuse to the surface of the composition, which is a very undesirable condition.

U.S. Pat. No. 4,374,224 relates to tree resistant compositions consisting of an ethylene polymer and an organic carboxylic ester having at least three carboxylic ester groups.

The combination of certain hydrocarboxysilanes and known long chain fatty acids, such as stearic, palmitic, phenylstearic useful as tree retardant additives for polymeric electrical insulation is disclosed in commonly assigned copending U.S. application Ser. No. 394,052 filed June 30, 1982, now U.S. Pat. No. 4,400,429.

Furthermore, acetophenone and dodecanol are also known to reduce tree growth in high voltage cables. However, acetophenone and dodecanol are volatile and diffuse out of the polymer over a period of time and for this reason are not totally satisfactory. Moreover, the incorporation of either acetophenone or dodecanol into the polymer is also difficult because of volatility.

SUMMARY OF THE INVENTION

It is one object of the present invention to provide novel substituted fatty acids and esters or alcohols derived therefrom particularly useful as water tree and electrical tree retardant additives.

Another object of this invention is to provide polymeric compositions containing said substituted fatty acids, esters or alcohols, which exhibit enhanced resistance to water treeing and electrical treeing.

Still another object of the present invention is to provide novel substituted fatty acids, particularly well suited as water tree and electrical tree retardants, which are not volatile and which will not diffuse out of the polymer which contains them.

These and other objects are accomplished herein by providing new compounds, useful as anti-treeing agents, having the general formula

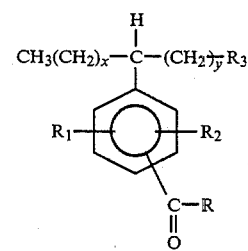

wherein R is a hydrocarbon radical having from 1 to 18 carbon atoms selected from the group consisting of alkyl, aryl or substituted aryl, cycloalkyl or substituted cycloalkyl, x and y total from about 5 to about 19, $R_1$ and $R_2$ are each independently hydrogen or $C_1$–$C_{18}$ alkyl, and $R_3$ is selected from the group consisting of COOH, COOR$_4$ and CH$_2$OH wherein R$_4$ is a hydrocarbon radical having from about 1 to 18 carbon atoms and selected from alkyl, cycloalkyl or substituted cycloalkyl, and aryl or substituted aryl.

DETAILED DESCRIPTION OF THE INVENTION

The substituted fatty acids of the present invention can be prepared by the reaction of an unsaturated fatty acid with benzene in the presence of a Lewis acid or mineral acid, such as sulfuric acid, to obtain the phenyl-substituted fatty acid. For example, when oleic acid is reacted with benzene, phenylstearic acid is produced. The phenyl-substituted fatty acid is then acylated with, for example, acetyl chloride or other appropriate acylating agent in the presence of a suitable catalyst, such as aluminum chloride, and in a suitable inert solvent, such as carbon tetrachloride, to obtain the novel products of this invention. Other mono-unsaturated fatty acids which may be used as starting materials for the preparation of the novel compounds of this invention include undecylenic acid, elaidic acid, erucic acid, and the like.

Esters of unsaturated fatty acids can also be reacted with benzene in the presence of a Lewis acid or mineral acid. The resulting product generally consists of a mixture of phenyl-substituted fatty acid and phenyl-substituted fatty acid ester which can then be acylated in the usual manner. The acylated phenyl-substituted fatty acid/ester may be used as such or may be converted totally to the acid product or totally to the ester product by techniques known to those skilled in the art. The ester products of this invention may also be obtained by reaction of the acylated phenyl-substituted fatty acid with an alcohol using conventional esterification techniques.

The novel compounds of the present invention can also be derived directly from the phenyl-substituted fatty acid or phenyl-substituted fatty acid ester, if such starting materials are available.

The substituted long chain alcohols of the present invention, i.e., wherein $R_3$ is CH$_2$OH, are prepared by first reducing the phenyl-substituted fatty acid or phenyl-substituted fatty acid ester in accordance with known reducing procedures and using conventional reducing agents, such as lithium aluminum hydride and the like. The phenyl-substituted alcohol is then reacted with at least two equivalents of the acylating agent, acetyl chloride or other appropriate acylating agent, in the presence of a suitable catalyst, such as aluminum chloride, to acylate the phenyl ring. Additionally, the alcohol group is converted to an ester. Subsequent saponification of the ester using a base, such as potassium hydroxide, converts the ester back to the desired acetylphenyl-substituted long-chain alcohol.

The novel compounds of the present invention obtained by the above-described procedures and useful as anti-treeing agents have the general formula

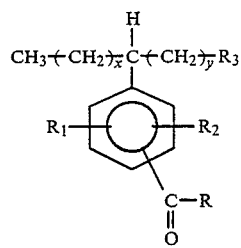

wherein R is a hydrocarbon radical having from about 1 to 18 carbon atoms selected from the group consisting of alkyl, aryl or substituted-aryl, cycloalkyl or substituted cycloalkyl, x and y total from about 5 to about 19, $R_1$ and $R_2$ are hydrogen or $C_{1-18}$ alkyl, and $R_3$ is selected from the group consisting of COOH, COOR$_4$, and CH$_2$OH wherein R$_4$ is a hydrocarbon group having from about 1-18 carbon atoms and selected from alkyl, aryl or substituted aryl, cycloalkyl or substituted cycloalkyl. Especially useful products of the invention are those where R is $C_{1-4}$ alkyl or phenyl, $R_1$ and $R_2$ are hydrogen or $C_{1-4}$ alkyl, and R$_4$ is a $C_{1-4}$ alkyl.

Specific compounds within the above general formula and which are included within the scope of the present invention include acetylphenylstearic acid, benzoylphenylstearic acid, methyl acetylphenylstearate, phenyl acetylphenylstearate, methyl benzoylphenylstearate, acetylphenylundecanoic acid, benzoylphenylundecanoic acid, methyl acetylphenylundecanoate, acetylphenylundecanol, acetylphenyloctadecanol (acetylphenylstearol), acetylphenyldocosanoic acid, benzoylphenyldocosanoic acid, methyl acetylphenyldocosanoate, and acetylphenyldocosanol.

In a further embodiment of the present invention, the afore-described substituted fatty acids are incorporated in polymer compositions to provide excellent tree retardant properties to the polymer.

In general the polymers suitable for the practice of this invention include any normally solid synthetic organic polymeric thermoplastic resin. Included are polyolefins and copolymers thereof, vinyls, olefin-vinyl copolymers, olefin-allyl copolymers, polyamides, acrylics, polystyrenes, cellulosics, polyesters and fluorocarbons.

The polyolefins include normally solid polymers of olefins, particularly mono-alpha-olefins, which comprise from about two to about six carbon atoms, e.g., polyethylene, polypropylene, polybutene, polyisobutylene, poly(4-methyl-pentene), and the like. Preferred poly-olefins are polyethylene and polypropylene. Polyethylene is especially preferred. Specific polyethylenes include linear low density polyethylene, high density polyethylene and low density polyethylene. An especially preferred polyethylene because of its demonstrated effectiveness is termed NA 310 and is sold by National Distillers and Chemical Company.

Copolymers of ethylene, and other compounds interpolymerizable with ethylene such as butene-1, pentene-1, styrene and the like may be employed. In general the copolymer will contain 50 weight percent or more ethylene. Other copolymers, such as ethylene-propylene rubber (EPR) and ethylene-propylene-diene monomer (EPDM) are also contemplated herein.

Suitable vinyl polymers include polyvinyl chloride, polyvinyl acetate, vinyl chloride/vinyl acetate copolymers, polyvinyl alcohol and polyvinyl acetal.

Suitable olefin-vinyl copolymers include ethylene-vinyl acetate, ethylene-vinyl propionate, ethylene-vinyl isobutyrate, ethylene-vinyl alcohol, ethylene-methyl acrylate, ethylene-ethyl acrylate, ethylene-ethyl methacrylate, and the like. In general the ethylene constitutes at least about 25 percent of the copolymer by weight.

Olefin-allyl copolymers include ethylene-allyl benzene, ethylene-allyl ether, ethylene-acrolein, and the like.

When it is desired to use a polymeric composition which can be crosslinked, crosslinking can be accomplished by any of the known procedures such as chemical means including peroxide crosslinking; by radiation using electron accelerators, gamma-rays, high energy radiation, such as X-rays, microwaves etc.; or by thermal crosslinking. The basic procedures for crosslinking polymers are extremely well known to the art and need not be described here in detail.

Conventional crosslinking agents such as organic peroxides may be suitably employed. Typical organic peroxide free radical generators include dicumyl peroxide; 2,5-bis(t-butylperoxy)-2,5-dimethylhexane; di-t-butyl peroxide; benzoyl peroxide; α, α'-bis (t-butyl peroxy) diisopropyl benzene and the like, as discussed in U.S. Pat. No. 3,287,312. The amount of organic peroxide, when employed, will range from about 0.5 to 5.0 percent by weight based on the total weight of the composition, or about 0.5 to 10 phr, preferably 3 to 6 phr.

Minor amounts of other additives may also be employed in conventional amounts to obtain the desired results. Conventional antioxidants such as the hindered phenols, polyquinolines and the like may be employed. Other ingredients that may be included are plasticizers, dyes, pigments, heat and light stabilizers, antistatic agents and the like.

The preferred compositions of this invention are generally unfilled polymer compositions. The term "unfilled" as applied to the instant composition shall mean a composition which contains less than 10 percent of a conventional polymer filler. For certain applications and to meet particular specifications the unfilled compositions herein may contain no filler. The preferred compositions of this invention may contain, therefore, 0 to less than 10 percent filler. When polymers such as ethylene-propylene rubber (EPR) and ethylene-propylene-diene monomer (EPDM) are employed however, from about 20 percent to about 30 percent filler are generally used. Such compositions are also intended to be within the scope of this invention. Accordingly, fillers, such as mineral fillers, may be employed to this extent in preparing the compositions of the invention.

The polymer compositions of this invention can be prepared by mixing the various ingredients. When the organic compound and the polymeric component are mixed together to form the instant compositions, the organic compound and polymeric component are homogeneously dispersed in each other. The order of mixing and specific procedure employed are not critical except to the extent that from the time the peroxide is added, if employed, the temperature is less than about 130° C. in order to prevent premature curing of the composition. This precaution, however, is conventional in the art.

The components may be mixed on a variety of apparatus including multi-roll mills, screw mills, continuous mixers, compounding extruders and Banbury mixers.

After being extruded onto wire or cable, or other substrate, the crosslinkable compositions are vulcanized at elevated temperatures, e.g., above about 180° C. using conventional vulcanizing procedures.

To provide the anti-treeing or electric tree retardant properties, the compounds of the present invention are generally added to the polymer in amounts which will be effective to inhibit water treeing and/or electrical treeing of the polymeric composition. Specifically, these amounts are from about 0.2 parts to about 5.0 parts based on 100 parts of base resin. Furthermore, it should be understood that the present compounds can be used alone or in combination with known anti-treeing compounds, such as amino silanes, vinyl trialkoxy silanes, epoxy-silanes, vinyl trisphenoxyethoxy silane, tin, phosphorous or titanium compounds of the hydrocarboxysilanes disclosed in the afore-mentioned copending U.S. application Ser. No. 394,052 incorporated herein by reference.

In order to determine the utility and effectiveness of the polymeric compositions of the present invention with regard to its inhibiting effect on the water treeing and the electrical treeing thereof, the compositions are evaluated by the use of accelerated tests.

Electrical tree tests are performed by using the method similar to that in IEEE Conference Paper No. C73, 257-3 1973 by E. J. McMahon and J. R. Perkins. Strips of material approximately 1-inch wide are cut from ¼-inch thick compression molded plaque. The block is machined to give a strip having parallel edges 1-inch apart. The strip is then cut into 1-inch square blocks. A blunt needle and a sharp needle are inserted into opposite parallel edges, at elevated temperatures, so that the points are ⅛-inch apart. Needle insertion and cooling of the sample are performed slowly to avoid inducing thermal or mechanical stresses in the specimen. The sharp needle has a tip diameter of about 0.0002-inch while the diameter of the blunt needle is 0.002-inch. Eight specimens are prepared and tested simultaneously for each composition. The electrical tree test is performed by energizing the sharp needle at 15 KV using a frequency of 60 Hz; the blunt needle is connected to ground. The time required for each of the eight specimens to fail by tree growth and subsequent electrical short is recorded. The time required for 50 percent of the samples to fail is employed to characterize the effectiveness of the tree retardant being evaluated.

The water tree test is performed using a procedure similar to that described in U.S. Pat. No. 4,144,202. A compression molded disc about 150 millimeters (mm.) in diameter having 10 conical depressions is prepared for each composition. The geometry of the disc and dimensions of the depressions are substantially the same as shown in U.S. Pat. No. 4,144,202. The base of the disc is sprayed with silver paint which serves as the ground electrode. An acrylic tube 6-inches long is clamped to the upper face forming a test cell. About 150 ml. of 0.01 N sodium chloride solution is poured into the cell and the air bubbles trapped on the surface of the sample are removed. A platinum wire ring is then immersed in the electrolyte and connected to the electrical supply which provides 5 KV at a frequency of 3 KHz. Samples are energized for 22 hours after which time they are removed from the test cell and washed with distilled water. The ten depressions are cut from the disc and stained to make the water trees more visible. Thin sections are obtained with a microtome, which are then examined microscopically (at 200×) and the tree size measured. Normally four discs are made for each sample so that the average tree size is calculated from forty individual measurements. In evaluating different tree retardants, the relative tree size is determined by comparing the average tree size obtained on a standard thermoplastic high voltage insulation material containing no tree retardant additives.

Various embodiments of the present invention will now be illustrated by reference to the following specific examples. It is to be understood, however, that such examples are presented for purposes of illustration only, and the present invention is in no way to be deemed as limited thereby. All parts and percentages are by weight unless otherwise noted.

EXAMPLE 1

PREPARATION OF ACETYLPHENYL-STEARIC ACID: A reactor equipped with a stirrer, thermometer, condenser and addition funnel was charged with 795 mls concentrated sulfuric acid (15 moles). The flask was immersed in an ice-bath, cooled to 0°–5° C., and benzene (1170 g; 15 moles) added slowly to the sulfuric acid while maintaining the temperature at 5° C. Oleic acid (847.2 g; 3 moles) was charged to the addition funnel and added slowly to the benzene-sulfuric acid mixture. The reaction temperature was maintained at 5°–10° C. When the oleic acid addition was completed, the cooling bath was removed and the reaction mixture was stirred for 1.5 hours.

The reaction mixture was quenched over ice and the benzene layer washed with water until the pH of the wash water was 4–5. Removal of the benzene afforded 95.6 percent yield of a crude product containing 82.2 percent phenylstearic acid by GLC. NMR was consistent with the structure. The crude product was distilled in a one-plate still to yield a heart cut containing 96.6 percent phenylstearic acid and 3.4 percent fatty acids. The acid value of the heart cut was 159.5 mg KOH/g (theory 155.6).

A 500 ml reaction vessel was charged with 200 mls freshly distilled carbon tetrachloride and the $CCl_4$ was cooled to 0°–5° C. Aluminum chloride (0.33 moles) was added, via Gooch tubing, to the $CCl_4$ over a period of 20 minutes. Acetyl chloride (0.35 mol) was added to an addition funnel and charged to the $CCl_4$-$AlCl_3$ mixture. Phenylstearic acid (0.125 moles) was then slowly added to the reaction mixture from an addition funnel while maintaining the temperature of the reaction mixture at 0°–5° C. The temperature was maintained at 0°–5° C. for one hour and at room temperature for an additional two hours. The evolution of HCl was observed.

The reaction mixture was quenched over 500 g of ice containing 70 mls concentrated HCl. The $CCl_4$ phase was separated and washed with water until the wash water was free of mineral acid. $CCl_4$ was removed and the crude yield was 48.7 g (96.7%) containing 89.4 percent acetylphenylstearic acid by GLC. The crude product was distilled in a short-path distillation apparatus and the fraction boiling at 257°–271° C. at 5 mm Hg pressure collected. NMR shows the product to be substituted at the para position. Two sets of aromatic peaks at 1.98–2.12 and 2.65–2.79 $\tau$, a singlet at 7.41 showing $CH_3$ protons and the normal fatty acid protons were observed. IR analysis showed acid at 1710 $cm^{-1}$ and ketone at 1680$^{-1}$ in addition to a small shoulder at 1740 $cm^{-1}$.

EXAMPLE 2

PREPARATION OF BENZOYLPHENYL-STEARIC ACID: To a one-liter glass reactor equipped with a mechanical stirrer, condenser, thermometer and addition funnel was charged 300 mls freshly distilled carbon tetrachloride. The flask and its contents were cooled to 0°–5° C. and 40 grams (0.30 mole) $AlCl_3$ added slowly. This was followed by the dropwise addition of 42 grams (0.30 mole) benzoyl chloride and then 26.9 grams (0.075 mole) phenylstearic acid. The mixture was maintained at 0°–5° C. for one hour with agitation and then allowed to warm to room temperature and stirred overnight. A yield of 40.4 percent crude benzoylphenylstearic acid was obtained upon work up of the reaction mixture.

EXAMPLE 3

PREPARATION OF METHYL ACETYL-PHENYLSTEARATE: A 250 ml flask equipped with a tube for subsurface addition was charged with 30.0 grams acetylphenylstearic acid, 0.1 gram p-toluenesulfonic acid and 100 mls toluene. This mixture was heated to 110°–125° C. and excess methanol slowly added via the subsurface tube over a period of about four hours. IR analysis of the reaction product confirmed the presence of ester and absence of ketal. The reaction was continued for an additional 15 hours during which time additional catalyst was added. Makeup methanol/toluene was added to the reactor as required.

The reaction mixture was shaken with dilute $H_2SO_4$ and the organic phase washed with dilute $Na_2CO_3$ and water until the wash water had a pH of approximately 7. The toluene was removed by evaporation to yield 33.7 grams crude product (AV=0) containing 94.5 percent methyl acetylphenylstearate by GLC analysis. Distillation of the crude product afforded 87 percent yield methyl acetylphenylstearate boiling at 210°–230° C. (0.05 mm Hg). The structure of the methyl acetylphenylstearate was confirmed by nuclear magnetic resonance spectroscopy.

EXAMPLE 4

PREPARATION OF ACETYLPHENYL-STEAROL: A one-liter flask equipped with addition funnel, thermometer, condenser and magnetic stirrer was charged with 400 mls anhydrous ethyl ether and 5.4 grams $LiAlH_4$ (0.14 mole). A solution of 50 grams phenylstearic acid in 200 mls ether was prepared and added via the addition funnel at a rate sufficient to maintain gentle reflux over a period of 1¼ hours. After refluxing at 35° C. overnight, the reaction mixture was cooled and the $LiAlH_4$ decomposed by treating with water and aqueous potassium hydroxide. After filtering, the filtrate was washed with water. Methanol and toluene were added to break the resulting emulsion and resolve the phases. Evaporation of the organic solvents afforded 44.9 grams (93.4% yield) phenylstearyl alcohol (B.P. 187°–209° C. at 0.25 mm Hg; zero acid value). The nuclear magnetic resonance spectrum of the product was consistent with the structure.

A quantitative yield of acetylphenylstearyl acetate was obtained from the Friedel-Crafts acylation of phenylstearyl alcohol with acetyl chloride in the presence of $AlCl_3$. GLC analysis of the product indicated 99.5 percent acetylphenylstearyl acetate and IR showed the disappearance of the hydroxyl band and appearance of two new carbonyl bands. NMR confirmed para substitution and two separate singlets for each methyl group next to the carbonyl.

The acetylphenylstearyl acetate (50.0 g) was refluxed for two hours in a solution of 9.76 grams KOH in 200 mls of methanol. The reaction product was worked up by: (1) acidification with dilute $H_2SO_4$, (2) dilution with water and extraction with toluene, and (3) washing the toluene free of acid. The crude product obtained by evaporation of the toluene solvent contained 98.9 percent acetylphenylstearol by GLC. IR of the crude showed a loss of acetate carbonyl and the appearance of alcohol. By distillation using a short-path column, 99+ percent pure acetylphenylstearol boiling at 217° C. (0.05 mm Hg) was obtained.

EXAMPLES 5-7

The same procedures described above were employed to obtain the following:

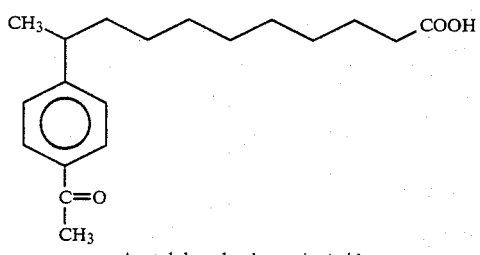

Acetylphenylundecanoic Acid

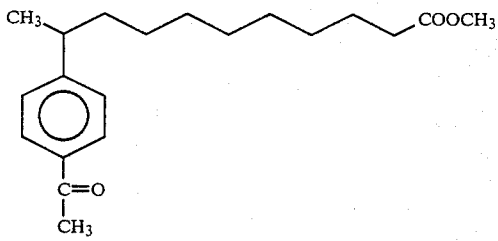

Methyl Acetylphenylundecanoate

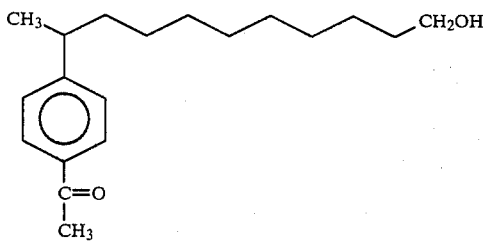

Acetylphenylundecanol

EXAMPLES 8-13

Compositions prepared by milling a commercial grade of polyethylene (NA 310) and the specified quantity of treeing additive were evaluated in accordance with the hereinbefore identified procedures. The test results are shown in the following Table.

TABLE

| Example | Composition* | Wet Tree Size μm | Needle Test $F_{50}$ Mins. |
|---|---|---|---|
| Control | NA 310 | 200 | 75 |
| 8 | acetylphenylstearic acid | 87 | 85 |
| 9 | acetylphenylstearyl alcohol | 66 | 180 |
| 10 | methyl acetylphenylstearate | 76 | 81 |
| 11 | acetylphenylundecanoic acid | 72 | 132 |
| 12 | acetylphenylundecanol | 59 | 126 |
| 13 | methyl acetylphenylundecanoate | 90 | 75 |

*Compositions contain 1.5% of additive in NA 310

Obviously, other modifications and variations of the present invention are possible in the light of the above teachings. It is, therefore, to be understood that changes may be made in the particular embodiments of this invention as defined by the appended claims.

We claim:

1. A compound having the general structure:

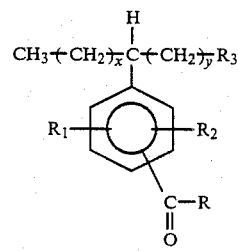

wherein R is a hydrocarbon radical having from 1 to 18 carbon atoms selected from the group consisting of alkyl, aryl, substituted aryl, cycloalkyl and substituted cycloalkyl, $R_1$ and $R_2$ are independently selected from the group consisting of hydrogen and $C_1-C_{18}$ alkyl, $R_3$ is selected from the group consisting of COOH, $COOR_4$ and $CH_2OH$, wherein $R_4$ is a hydrocarbon radical having from 1 to 18 carbon atoms and selected from the group consisting of alkyl, aryl, substituted aryl, cycloalkyl and substituted cycloalkyl, and x and y are integers such that the total of $x+y$ is from about 5 to about 19.

2. A compound as defined in claim 1 wherein $R_1$ and $R_2$ are hydrogen.

3. A compound as defined in claim 1 wherein $R_1$ and $R_2$ are hydrogen and R is alkyl or aryl.

4. Acetylphenylstearic acid.

5. Benzoylphenylstearic acid.

6. Acetylphenylundecanoic acid.

7. A polymeric composition having enhanced resistance to water treeing and electrical treeing comprising an intimate admixture of a polymeric component and an effective water treeing and/or electrical treeing inhibitor amount of a compound having the general structure:

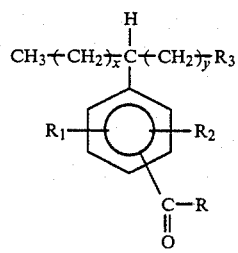

wherein R is a hydrocarbon radical having from 1 to 18 carbon atoms selected from the group consisting of alkyl, aryl, substituted aryl, cycloalkyl and substituted cycloalkyl, $R_1$ and $R_2$ are independently selected from the group consisting of hydrogen and $C_1$–$C_{18}$ alkyl, $R_3$ is selected from the group consisting of COOH, $COOR_4$ and $CH_2OH$ wherein $R_4$ is a hydrocarbon radical having from 1 to 18 carbon atoms and selected from the group consisting of alkyl, aryl, substituted aryl, cycloalkyl and substituted cycloalkyl, and x and y are integers such that the total of x+y is from about 5 to about 19.

8. A method of stabilizing a polymeric insulated electrical conductor against water treeing and electrical treeing which comprises coating an electrical conductor with an insulating effective amount of a polymeric insulating composition, said composition comprising an intimate admixture of a polymeric component and an effective water treeing and/or electrical treeing inhibitor amount of a compound having the general structure:

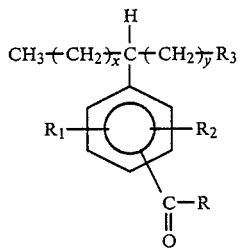

wherein R is a hydrocarbon radical having from 1 to 18 carbon atoms selected from the group consisting of alkyl, aryl, substituted aryl, cycloalkyl and substituted cycloalkyl, $R_1$ and $R_2$ are independently selected from the group consisting of hydrogen and $C_1$–$C_{18}$ alkyl, $R_3$ is selected from the group consisting of COOH, $COOR_4$ and $CH_2OH$, wherein $R_4$ is a hydrocarbon radical having from 1 to 18 carbon atoms and selected from the group consisting of alkyl, aryl, substituted aryl, cycloalkyl and substituted cycloalkyl, and x and y are integers such that the total of x+y is from about 5 to about 19.

9. A polymeric composition as in claim 7 wherein $R_1$ and $R_2$ are hydrogen.

10. A polymeric composition as in claim 9 wherein R is alkyl or aryl.

11. A polymeric composition as in claim 7 wherein said inhibitor compound is acetylphenylstearic acid.

12. A polymeric composition as in claim 7 wherein said inhibitor compound is benzoylphenylstearic acid.

13. A polymeric composition as in claim 7 wherein said inhibitor compound is acetylphenylundecanoic acid.

* * * * *